United States Patent
Haraikawa et al.

(10) Patent No.: US 10,144,193 B2
(45) Date of Patent: Dec. 4, 2018

(54) TEXTILE STRUCTURE

(71) Applicants: Kinpo Electronics, Inc., New Taipei (TW); Cal-Comp Electronics & Communications Company Limited, New Taipei (TW)

(72) Inventors: Koichi Haraikawa, New Taipei (TW); Jen-Chien Chien, New Taipei (TW); Tsai-Chieh Hsu, New Taipei (TW); Chih-Wei Liu, New Taipei (TW)

(73) Assignees: Kinpo Electronics, Inc., New Taipei (TW); Cal-Comp Electronics & Communications Company Limited, New Taipei (TW)

( * ) Notice: Subject to any disclaimer, the term of this patent is extended or adjusted under 35 U.S.C. 154(b) by 646 days.

(21) Appl. No.: 14/598,235

(22) Filed: Jan. 16, 2015

(65) Prior Publication Data
US 2016/0144596 A1 May 26, 2016

(30) Foreign Application Priority Data
Nov. 26, 2014 (TW) .............................. 103140965 A

(51) Int. Cl.
*B32B 5/26* (2006.01)
*B32B 3/26* (2006.01)
(Continued)

(52) U.S. Cl.
CPC .............. *B32B 5/26* (2013.01); *A61B 5/6804* (2013.01); *B32B 3/266* (2013.01); *B32B 5/06* (2013.01);
(Continued)

(58) Field of Classification Search
CPC ...................................................... B32B 5/26
See application file for complete search history.

(56) References Cited

U.S. PATENT DOCUMENTS

2007/0299325 A1 12/2007 Farrell et al.
2012/0238910 A1 9/2012 Nordstrom
(Continued)

FOREIGN PATENT DOCUMENTS

CN 201253206 6/2009
CN 202654120 1/2013
(Continued)

OTHER PUBLICATIONS

"Office Action of Taiwan Counterpart Application", dated Sep. 22, 2015, p. 1-p. 12.
"Office Action of Europe Counterpart Application" , dated Jul. 15, 2016, p. 1-p. 9.
"Office Action of China Counterpart Application," dated Jun. 20, 2017, p. 1-p. 8.
(Continued)

*Primary Examiner* — Andrew T Piziali
(74) *Attorney, Agent, or Firm* — JCIPRNET

(57) ABSTRACT

A textile structure adapted to be electrically connected to an electronic device is provided. The textile structure includes a first fabric layer, a second fabric layer, and a third fabric layer. The second fabric layer is electrically conductive. The first, the second, and the third fabric layers are combined with each other, and the second fabric layer is located between the first and the third fabric layers. The third fabric layer has an opening covered by the second fabric layer, and a portion of the second fabric layer is exposed from the third fabric layer through the opening. The electronic device is electrically connected to the second fabric layer, and a junction between the electronic device and the second fabric layer is far away from the opening.

22 Claims, 2 Drawing Sheets

(51) Int. Cl.
    *A61B 5/00*           (2006.01)
    *B32B 5/06*           (2006.01)
    *B32B 5/22*           (2006.01)
    *B32B 7/12*           (2006.01)
    *B32B 25/08*         (2006.01)
    *B32B 25/10*         (2006.01)
    *B32B 25/14*         (2006.01)
    *B32B 27/12*         (2006.01)
    *A41D 1/00*          (2018.01)

(52) U.S. Cl.
    CPC ............... *B32B 5/22* (2013.01); *B32B 7/12* (2013.01); *B32B 25/08* (2013.01); *B32B 25/10* (2013.01); *B32B 25/14* (2013.01); *B32B 27/12* (2013.01); *A41D 1/002* (2013.01); *B32B 2262/103* (2013.01); *B32B 2262/106* (2013.01); *B32B 2307/202* (2013.01); *B32B 2307/51* (2013.01); *B32B 2307/724* (2013.01); *B32B 2307/726* (2013.01); *B32B 2307/73* (2013.01); *B32B 2457/00* (2013.01)

(56) References Cited

U.S. PATENT DOCUMENTS

2013/0225966 A1     8/2013     Macia Barber et al.
2014/0039292 A1     2/2014     Su et al.

FOREIGN PATENT DOCUMENTS

| | | |
|---|---|---|
| CN | 202699125 | 1/2013 |
| CN | 203016942 | 6/2013 |
| JP | 3178230 | 6/2001 |
| JP | 3189103 | 7/2001 |
| JP | 2011036524 | 2/2011 |
| JP | 2014500077 | 1/2014 |
| TW | 200946728 | 11/2009 |
| TW | M458941 | 8/2013 |
| TW | M463109 | 10/2013 |

OTHER PUBLICATIONS

"Office Action of Japan Counterpart Application", dated Aug. 6, 2018, p. 1-p. 6.

TEXTILE STRUCTURE

CROSS-REFERENCE TO RELATED APPLICATION

This application claims the priority benefit of Taiwan application serial no. 103140965, filed on Nov. 26, 2014. The entirety of the above-mentioned patent application is hereby incorporated by reference herein and made a part of this specification.

BACKGROUND

1. Technical Field

The disclosure generally relates to a textile structure, and more particularly, to a textile structure capable of being connected with an electronic device.

2. Description of Related Art

In recent year, with the rapid changes in electronic technology, people become more particular about living comfort and health, and thus development of intelligent clothing or related wearable items have gradually received increasing attention. Taking the intelligent clothing for an example, with the functions of the intelligent clothing, a user is only required to wear on the intelligent clothing for achieving specific functions, such as physiological condition sensing or monitoring, heating, cooling and so forth, without additionally using any external device, thereby greatly improving an ease of use.

Nevertheless, as limited by a condition that a sensing electrode must be corresponded to a specific location of human body, a conductive wire or a conductive ribbon is required to be used as a bridging structure between the sensing electrode and the external electronic device for providing electrical connection. As a result, the conductive wire or the conductive ribbon has to be additionally disposed (sewed) on the intelligent clothing. However, the conductive wire or the conductive ribbon is prone to swing along with the intelligent clothing that is worn on the human body, and thereby may influence an electrical signal transmission thereof and may even become malfunctioned due to intolerance to human movement or cleansing. Therefore, how to provide a connection structure between the sensing electrode and the electronic device has become a relevant topic for those skilled in the art of the related field.

SUMMARY

The disclosure provides a textile structure, which is connected between an electronic device and an opening of a fabric layer through using an electrically conductive fabric layer, and thereby enhances the degree of freedom thereof in connecting with the electronic device.

The textile structure of the disclosure is adapted to be electrically connected to the electronic device. The textile structure includes a first fabric layer, a second fabric layer and a third fabric layer. The second fabric layer is electrically conductive. The first fabric layer, the second fabric layer and the third fabric layer are combined with each other, and the second fabric layer is located between the first fabric layer and the third fabric layer. The third fabric layer has an opening covered by the second fabric layer, and a portion of the second fabric layer is exposed from the opening. The electronic device is electrically connected to the second fabric layer, and a junction between the electronic device and the second fabric layer is far away from the opening.

The textile structure of the disclosure includes a first fabric layer, a second fabric layer, a third fabric layer and a fourth fabric layer that are combined with each other. The second fabric layer is electrically conductive. The third fabric layer has an opening. The second fabric layer is located between the first fabric layer and the third fabric layer, and the fourth fabric layer is located between the second fabric layer and the first fabric layer. The second fabric layer covers the opening, and a portion of the second fabric layer is exposed from the opening. The fourth fabric layer is corresponded to the opening, and a water absorbability of the fourth fabric layer is greater than a water absorbability of the second fabric layer.

In view of the foregoing, by disposing the electrically conductive second fabric layer between the first fabric layer and the third fabric layer and by enabling an end of the second fabric layer to expose the textile structure out of the opening of the third fabric layer while another end of the second fabric layer being electrically connected to the electronic device, the textile structure can be used to sense different locations whereby electrodes of physiological signals can locate with an size extension of the second fabric layer. Meanwhile, the second fabric layer is sewed or interwoven between the first fabric layer and the third fabric layer, and thus can be bended or moved along with the textile structure without affecting the transmission of an electrical signal thereof. The textile structure is able to provide higher degree of freedoms of electrical connection range and applicability.

In order to make the aforementioned and other features and advantages of the disclosure more comprehensible, several embodiments accompanied with figures are described in detail below.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

DESCRIPTION OF THE EMBODIMENTS

Figure 1:
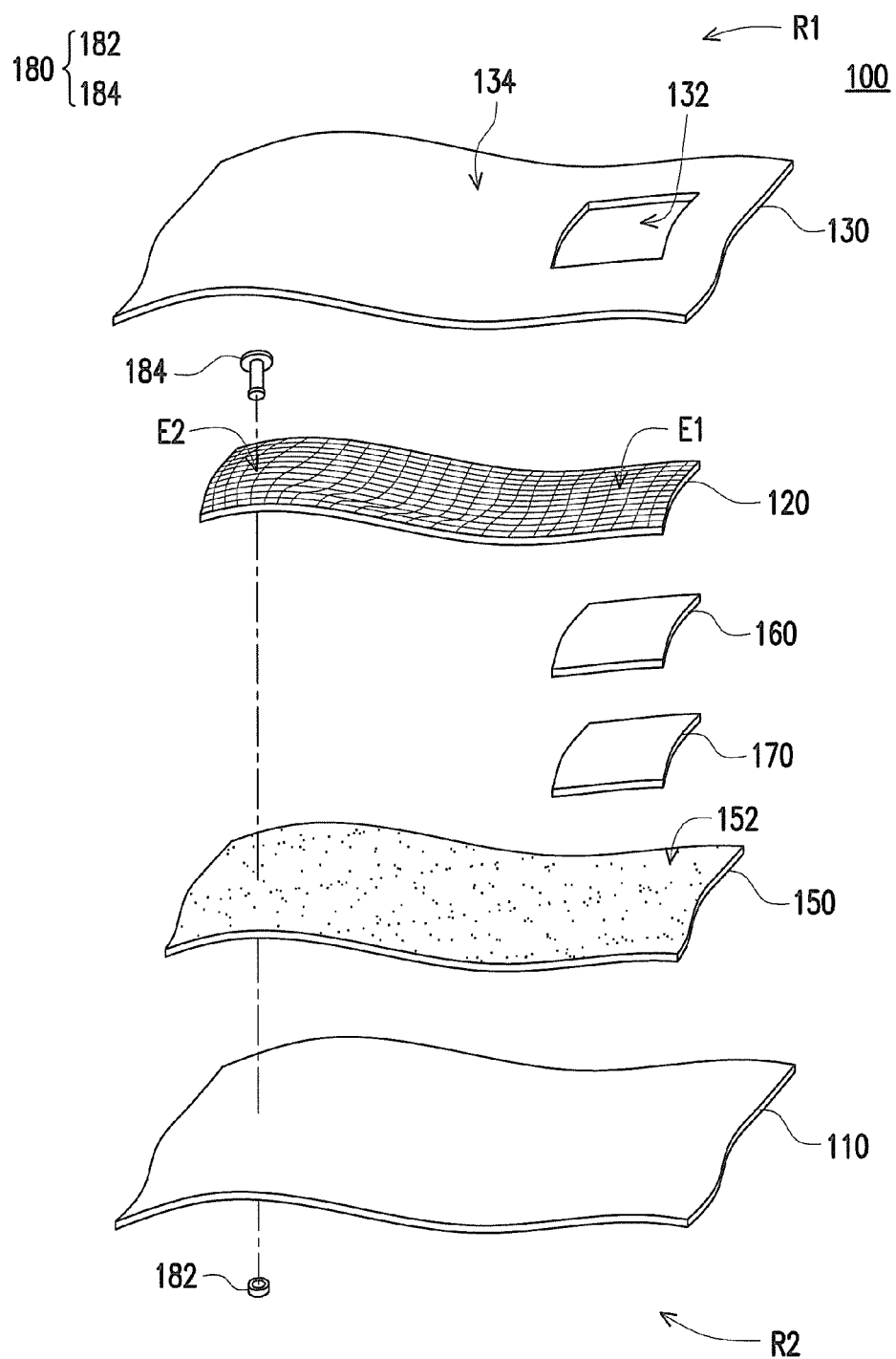
FIG. 1 is an exploded diagram illustrating a textile structure according to an embodiment of the disclosure.
Figure 2:
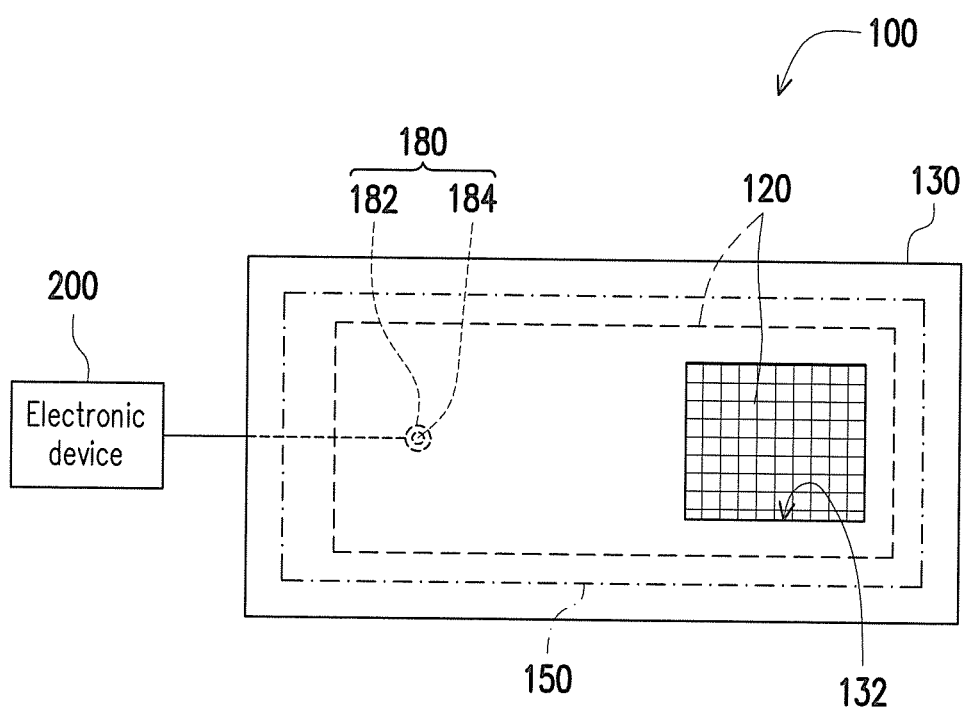
FIG. 2 is a top view of the textile structure shown in FIG. 1 after being combined.

FIG. 1 is an exploded diagram illustrating a textile structure according to an embodiment of the disclosure. FIG. 2 is a top view of the textile structure shown in FIG. 1 after being combined, which simultaneously shows an electrical connection relationship between the textile structure and an electronic device, but does not limit the location of the electronic device relative to the textile structure. Referring to FIG. 1 and FIG. 2 at the same time, in the present embodiment, a textile structure 100 is applicable as any clothing or item that can be worn on a living being (or human body), and has an inner side R1 and an outer side R2, wherein the inner side R1 is in contact with the body of the living being, and the outer side is adapted to be disposed with an electronic device 200; and concurrently, relevant biological information of the living being may be obtained by electrically connecting the textile structure 100 to the electronic device 200. Taking the human body for an example (the subsequent embodiments are also described through using the human body), when wearing the clothing or item containing the textile structure 100, physiological states of the human body, such as heartbeat, breathing, body temperature and so forth, can thus be obtained.

In the present embodiment. the textile structure 100 includes a first fabric layer 110, a second fabric layer 120 and a third fabric layer 130, wherein the first fabric layer 110, the second fabric layer 120 and the third fabric layer 130 are combined with each other by means of sewing or interwoven or by means of hot pressing or adhering through using hot melt glue, and the second fabric layer 120 is electrically conductive and located between the third fabric layer 130 and the first fabric layer 110. The third fabric layer 130 has an opening 132, and the second fabric layer 120 covers the opening 132, such that a portion of the second fabric layer 120 is exposed out of the third fabric layer 130 from the opening 132; and therefore, the exposed portion of the second fabric layer 120 can be used as an electrode contacting the human body. In other words, by controlling the size of the opening 132, an area of the second fabric layer 120 that is actually in contact with the human body may be controlled.

Moreover, the electronic device 200 is electrically connected to the second fabric layer 120, and a junction therebetween is far away from the opening 132 of the third fabric layer 130. Hence, the second fabric layer 120 located between the first fabric layer 110 and the third fabric layer 130 can simultaneously be used as the electrode in contact with the human body and a conductive wire connected to the electronic device 200. As a result, the textile structure 100 of the present embodiment does not require to additionally be disposed with a conductive wire or a conductive ribbon, and can directed achieved the electrical connection effect through using the second fabric layer 120, thereby increasing the degree of freedom for the textile structure 100 in terms of electrical connection while also lowering the production costs for additionally disposing a conductive wire.

Furthermore, the first fabric layer 110 is substantially made of the same material as the wearable clothing or item, or is namely a part of the clothing (item) which is being used as a base for bearing other components. The second fabric layer 120 is, for example, a stainless steel fabric, a silver fabric or a carbon fiber fabric, and has water absorbability; and therefore, the second fabric layer 120 may maintain its electrically conductivity with the human body when contacting the human body through the opening 132 while also being used as a bridging structure for electrically connecting between the electronic device 200 and the human body. Namely, the second fabric layer 120 has a first end E1 and a second end E2 that are opposite to and far away from each other, wherein the first end E1 electrically contacts the human body through the opening 132, and the second end E2 of the second fabric layer 120 is electrically connected to the electronic device 200.

The third fabric layer 130 is constituted of hydrophobic and air permeable material, and is not electrically conductive. In the textile structure 100, the third fabric layer 130 is used a component directly in contact with the human body, and thus is required to provide an electrical isolation effect between the second fabric layer 120 and the human body. Namely, in order to ensure that the second fabric layer 120 would not be influenced during a process of electrical signal transmission by the electrical conductivity between the first end E1 and the second end E2 thereof due to the second fabric layer 120 being in contact with the human body, the third fabric layer 130 must prevent the water in the second fabric layer 120 from being lost or evaporated due to the third fabric layer 130 while providing the human body with comfortable feeling with its air permeability.

In addition, in the present embodiment, the textile structure 100 further includes a thin film 150, which is hydrophobic and disposed between the first fabric layer 110 and the second fabric layer 120, wherein a material thereof may, for example, be plastic, thermoplastic polyurethane elastomer (TPU) or polyurethane (PU). The thin film 150 can be combined between the first fabric layer 110 and the third fabric layer 130 by means of hot pressing. Further, an area of the second fabric layer 120, which is greater than the opening 132 and covers the opening 132, is substantially smaller than that of the thin film 150 and the third fabric layer 130. In other words, the second fabric layer 120 is being sealed between the thin film 150 and the third fabric layer 130, and can only expose the textile structure 100 from the opening 132, so that water can be maintained in the second fabric layer 120. Similarly, the thin film 150 has vent holes 152 for improving a circulation effect of the air and enabling the textile structure 100 to be more comfortable in wearing.

The textile structure 100 of the present embodiment further includes a water absorbing elastic layer 170 and a fourth fabric layer 160, wherein the water absorbing elastic layer 170 is disposed between the second fabric layer 120 and the thin film 150, and the water absorbing elastic layer 170 is corresponded to the opening 132 and covered by the opening 132 (namely, an area of the water absorbing elastic layer 170 is smaller than an area of the opening 132). Moreover, the water absorbing elastic layer 170 is thicker than the fabric layers in terms of structural thickness, and thus the second fabric layer 120 as being pressed against by the water absorbing elastic layer 170 is partially protruded out of the opening 132. In other words, after the components shown in FIG. 1 are combined with each other, the second fabric layer 120 is protruded out of a surface 134 of the third fabric layer 130 due to being pressed against by the water absorbing elastic layer 170. Herein, a material of the water absorbing elastic layer 170 is an elastic rubber, and more preferably being polyvinyl alcohol (PVA), neoprene, ethylene vinyl acetate (EVA), polyvinyl butyral (PVB) or polyurethane, which contains a lot of water for enabling the second fabric layer 120 to maintain moisture, is capable of increasing a fitting degree between the first end E1 of the second fabric layer 120 and the human body with its elastic material properties, and provides a cushion effect when the second fabric layer 120 contacts the human body, simultaneously.

The fourth fabric layer 160 is disposed between the second fabric layer 120 and the water absorbing elastic layer 170, and the fourth fabric layer 160 is, for example, a cotton cloth or a PVB water absorbent cloth, wherein a water absorbability thereof is greater than the water absorbability of the second fabric layer 120. This is because the water absorbability of the second fabric layer 120, such as being a metal fiber or a carbon fiber, is limited, and thus the second fabric layer 120 is prone to loss water when being in contact with the human body or other fabrics. Consequently, in addition to guiding the water from the water absorbing elastic layer 170 to the second fabric layer 120 via a capillary action of the fourth fabric layer 160, certain amount of water may be also be retained for later supply to the second fabric layer 120, thereby preventing the water from being lost rapidly.

On the other hand, the textile structure 100 further includes a fastener 180, which at least penetrates and holds together the first fabric layer 110 and the second fabric layer 120. Furthermore, the fastener 180 is electrically conductive and includes a retaining ring 182 and a rivet 184; and after the rivet 184 penetrates the first fabric layer 110 and the second fabric layer 120 to combine with the retaining ring 182, the fabric layers can lap joint together with each other. The electronic device 200 is electrically connected with the second fabric layer 120 via the fastener 180, and thereby can sense the physiological conditions of the human body. Herein, the disclosure does not intend to limit the forms of the fastener 180 (the rivet 184 and the retaining ring 182); for instance, in an embodiment (not shown), the fastener 180 can be any one of commonly used male and female clothing buckles (such as a male (female) snap buckle) or male and female medical buckles (such as a male (female) medical electrode buckle).

Moreover, in another embedment (not shown), during an electrical conduction process of fastener, there may further exist an insulating layer between the fastener 180 and the fabric layer that is not used for electrical conduction, so that the fastener 180 can be partially insulated from the fabric layers, thereby allowing the fastener 180 to be electrically connected with the electronic device more tightly without being exposed or influenced.

In summary, in the embodiments of the disclosure, by disposing the electrically conductive second fabric layer between the first fabric layer and the third fabric layer and by enabling one end of the second fabric layer to expose the textile structure out of the opening of the third fabric layer while another end of the second fabric layer being electrically connected to the electronic device, the textile structure can be used to sense different locations whereby the electrodes of physiological signals can locate with an size extension of the second fabric layer. As a result, the externally connected electronic device does not have to be restricted by sensing locations, thereby increasing the degree of freedom for the textile structure in terms of electrical connection.

Moreover, the second fabric layer is substantially sealed between the thin film and the third fabric layer with the fourth fabric layer and the water absorbing elastic layer, and thus the water absorbing elastic layer, with its characteristics in thickness, can press against the second fabric layer, so as to enable the second fabric layer to protrude out of the opening. In addition, since the water absorbability of the fourth fabric layer is greater than the water absorbability of the second fabric layer, the fourth fabric layer can transfer the water from the water absorbing elastic layer to the second fabric layer with a capillary phenomenon thereof, and thereby achieves an effect of maintain the moisture of the second fabric layer.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims and their equivalents.

What is claimed is:

1. A textile structure, adapted to be electrically connected to an electronic device, the textile structure comprising:
   a first fabric layer;
   a second fabric layer, being electrically conductive;
   a film, disposed between the first fabric layer and the second fabric layer, and the film being hydrophobic and having vent holes for providing air permeability; and
   a third fabric layer, wherein the first fabric layer, the second fabric layer and the third fabric layer are combined with each other, the second fabric layer is located between the first fabric layer and the third fabric layer, the third fabric layer has an opening covered by the second fabric layer, and a portion of the second fabric layer is exposed from the opening,
   wherein the second fabric layer is configured to be electrically connected to the electronic device, and a junction between the electronic device and the second fabric layer is separated from the opening,
   wherein the second fabric layer is disposed between the third fabric layer and the film.

2. The textile structure as recited in claim 1, wherein the first fabric layer, the second fabric layer and the third fabric layer are combined with each other by means of sewing, hot pressing or adhering.

3. The textile structure as recited in claim 1, wherein the second fabric layer is a stainless steel fabric, a silver fabric or a carbon fiber fabric.

4. The textile structure as recited in claim 1, wherein the third fabric layer is air permeable.

5. The textile structure as recited in claim 1, wherein the third fabric layer is hydrophobic.

6. The textile structure as recited in claim 1, wherein the film is a plastic material, and is combined between the first fabric layer and the third fabric layer by means of hot pressing.

7. The textile structure as recited in claim 1, wherein an area of the second fabric layer is smaller than or equal to an area of the film.

8. The textile structure as recited in claim 1, further comprising:
   a fastener, penetrating and at least holding together the first fabric layer and the second fabric layer, and the fastener being electrically connected to the electronic device.

9. The textile structure as recited in claim 1, further comprising:
   a water absorbing elastic layer, disposed between the second fabric layer and the film, wherein the water absorbing elastic layer has an area substantially corresponding to the opening and covered by the opening, and the second fabric layer as being pressed against by the water absorbing elastic layer partially protrudes out of the opening.

10. The textile structure as recited in claim 9, wherein a material of the water absorbing elastic layer comprises an elastic rubber among polyvinyl alcohol (PVA), neoprene, ethylene vinyl acetate (EVA), polyvinyl butyral (PVB) and polyurethane (PU).

11. The textile structure as recited in claim 9, further comprising:
   a fourth fabric layer, disposed between the second fabric layer and the water absorbing elastic layer, and a water absorbability of the fourth fabric layer being greater than a water absorbability of the second fabric layer.

12. A textile structure, comprising:
   a first fabric layer;
   a second fabric layer, being electrically conductive;
   a third fabric layer, having an opening;
   a fourth fabric layer, wherein the first fabric layer, the second fabric layer, the third fabric layer and the fourth fabric layer are combined with each other, the second fabric layer is located between the first fabric layer and the third fabric layer, the fourth fabric layer is located between the second fabric layer and the first fabric layer, the opening is covered by the second fabric layer, a portion of the second fabric layer is exposed from the opening, the fourth fabric layer has an area substantially corresponding to the opening, and a water absorbability of the fourth fabric layer is greater than a water absorbability of the second fabric layer; and a film, disposed between the first fabric layer and the fourth fabric layer, and the film being hydrophobic and having vent holes for providing air permeability, wherein the second fabric layer is disposed between the third fabric layer and the film.

13. The textile structure as recited in claim 12, wherein the second fabric layer is configured to be electrically connected to an electronic device, and a junction between the electronic device and the second fabric layer is separated, from the opening.

14. The textile structure as recited in claim 12, wherein the first fabric layer, the second fabric layer, the third fabric layer and the fourth fabric layer are combined with each other by means of sewing or hot pressing.

15. The textile structure as recited in claim 12, wherein the second fabric layer is a stainless steel fabric, a silver fabric or a carbon fiber fabric.

16. The textile structure as recited in claim 12, wherein the third fabric layer is air permeable.

17. The textile structure as recited in claim 12, wherein the third fabric layer is hydrophobic.

18. The textile structure as recited in claim 12, wherein the film is a plastic material, and is combined between the first fabric layer and the third fabric layer by means of hot pressing.

19. The textile structure as recited in claim 12, wherein an area of the second fabric layer is smaller than or equal to an area of the film.

20. The textile structure as recited in claim 12, further comprising:

a fastener, penetrating and at least holding together the first fabric layer and the second fabric layer, and the fastener being electrically connected to the electronic device.

21. The textile structure as recited in claim 12, further comprising:

a water absorbing elastic layer, disposed between the fourth fabric layer and the film, wherein the water absorbing elastic layer has an area substantially corresponding to the opening and covered by the opening, and the second fabric layer as being pressed against by the water absorbing elastic layer partially protrudes out of the opening.

22. The textile structure as recited in claim 21, wherein a material of the water absorbing elastic layer comprises an elastic rubber among polyvinyl alcohol (PVA), neoprene, ethylene vinyl acetate (EVA), polyvinyl butyral (PVB) and polyurethane (PU).

* * * * *